United States Patent
Al Shail et al.

(10) Patent No.: US 10,231,765 B2
(45) Date of Patent: *Mar. 19, 2019

(54) VERTEBRAL FIXATION DEVICE

(71) Applicant: King Faisal Specialist Hospital and Research Centre, Riyadh (SA)

(72) Inventors: Essam Al Shail, Riyadh (SA); Falah Redha, Bern (CH)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/089,560

(22) Filed: Apr. 3, 2016

(65) Prior Publication Data

US 2016/0213404 A1    Jul. 28, 2016

Related U.S. Application Data

(63) Continuation of application No. 14/265,978, filed on Apr. 30, 2014, now Pat. No. 9,402,666.

(51) Int. Cl.
*A61B 17/70* (2006.01)
*A61B 17/80* (2006.01)

(52) U.S. Cl.
CPC ...... *A61B 17/8042* (2013.01); *A61B 17/7032* (2013.01); *A61B 17/7053* (2013.01); *A61B 17/7059* (2013.01)

(58) Field of Classification Search
USPC .................................................. 606/74, 263
See application file for complete search history.

(56) References Cited

U.S. PATENT DOCUMENTS

| | | | |
|---|---|---|---|
| 6,443,955 B1 | 9/2002 | Ahrend et al. | |
| 6,514,255 B1 * | 2/2003 | Ferree | A61B 17/7053 606/103 |
| 7,481,828 B2 | 1/2009 | Mazda et al. | |
| 8,162,946 B2 | 4/2012 | Baccelli et al. | |
| 8,403,930 B2 | 3/2013 | Chico Roca | |
| 8,430,918 B2 | 4/2013 | Baccelli et al. | |
| 9,023,087 B2 * | 5/2015 | Frankel | A61B 17/7032 606/251 |
| 2009/0248077 A1 | 10/2009 | Johns | |
| 2009/0292317 A1 | 11/2009 | Belliard | |

(Continued)

*Primary Examiner* — Jan Christopher Merene
(74) *Attorney, Agent, or Firm* — Saliwanchik, Lloyd & Eisenschenk (57) ABSTRACT

A spinal fixation device is provided, comprising a body member having a first side and an opposite second side, and an elongate flexible strap having a first section and a second section. The first section of the strap is attached or attachable to attachment means of the body member arranged at a first location thereof. The second section of the strap is sized and shaped to pass through a passageway arranged at a second location of the body member. The strap has a series of teeth and the passageway of the body member has a latch configured for engaging one of the teeth. The teeth and the latch are configured to allow a movement of the second section of the strap through the passageway in a tightening direction from the first side to the second side of the body member, and to prevent a movement of the second section in the opposite direction.

18 Claims, 10 Drawing Sheets

(56) References Cited

U.S. PATENT DOCUMENTS

| | | | |
|---|---|---|---|
| 2010/0160981 A1* | 6/2010 | Butler | A61B 17/7037 606/308 |
| 2011/0106178 A1* | 5/2011 | Schwab | A61B 17/7032 606/308 |
| 2012/0130373 A1* | 5/2012 | Larroque-Lahitette | A61B 17/7001 606/74 |
| 2013/0041410 A1 | 2/2013 | Hestad et al. | |

* cited by examiner

VERTEBRAL FIXATION DEVICE

CROSS-REFERENCE TO A RELATED APPLICATION

This application is a Continuation Application of co-pending application Ser. No. 14/265,978, filed Apr. 30, 2014, now U.S. Pat. No. 9,402,666, which is incorporated herein by reference in its entirety.

FIELD OF THE INVENTION

The present disclosure relates to a vertebral fixation device. In more detail, the present disclosure relates to a vertebral fixation device having a body member and a strap that is configured for being mounted around a lamina of a vertebra, such as, e.g., a human vertebra.

BACKGROUND OF THE INVENTION

Vertebral fixation, also known as spinal fixation, is a neurosurgical procedure, in which two or more vertebrae are anchored to each other through a vertebral fixation device. It is an aim of such a neurosurgical procedure to reduce vertebral mobility and thus avoid possible damage to the spinal cord and/or the spinal roots. Indications for such a procedure are, amongst others, degenerative disk disease, spondylolisthesis, fracture, dislocation, spinal stenosis, fracture with instability, occipito-cervical dislocation, tumors and a revision of previous cervical spine surgery.

Common devices used to achieve vertebral fixation comprise permanent rigid or semi-rigid prostheses made of titanium. Known devices may include rods, plates, screws and various combinations thereof.

The medical community currently uses several different techniques for stabilizing the posterior region of the spine. The most radical of these techniques is spinal fusion. In recent years, spinal surgeons have begun to rely more heavily on mechanical implants which provide increased stability without so severely limiting the recipient's range of motion. A number of devices have been developed that allow the recipients an almost natural range of motion while still providing support. However, in many cases, the support offered by such devices is insufficient, leaving the physician with few other choices than spinal fusion.

Figure 1:
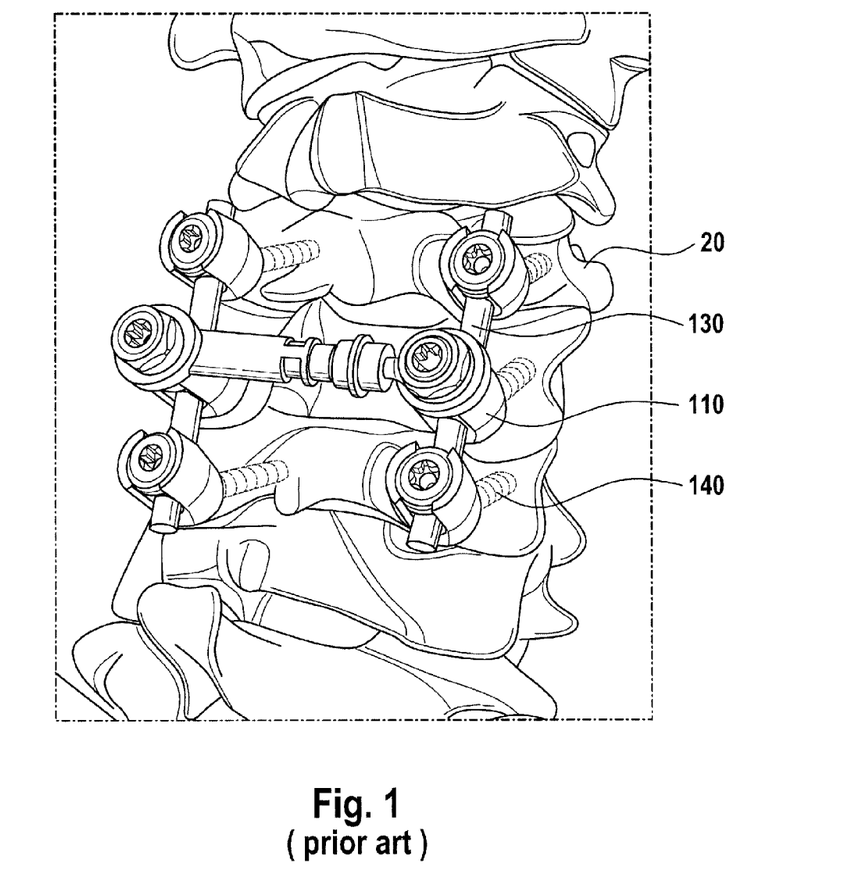
FIG. 1 shows a spinal fixation system known in the art.

A known device used to achieve vertebral fixation is shown exemplarily in FIG. 1. In FIG. 1, three vertebrae 20 are anchored to each other through a system comprising six spinal fixation devices 110. Two devices 110 are attached to each vertebra to be anchored. Each device 110 is attached to a respective vertebra by means of a screw 140. The devices 110 attached to different vertebrae 20 are coupled to each other via a connecting rod 130.

Figure 2:
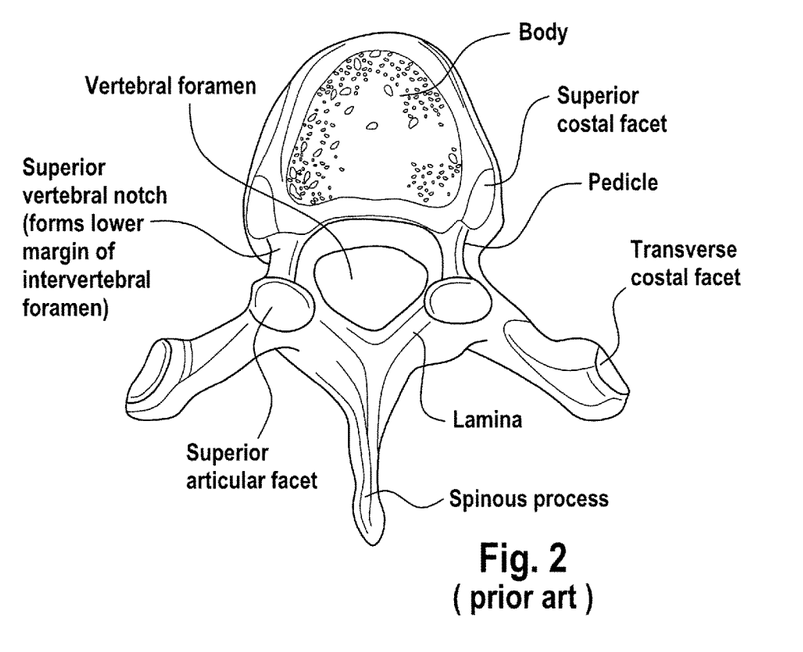
FIG. 2 shows a top view of a human vertebra.
Figure 3:
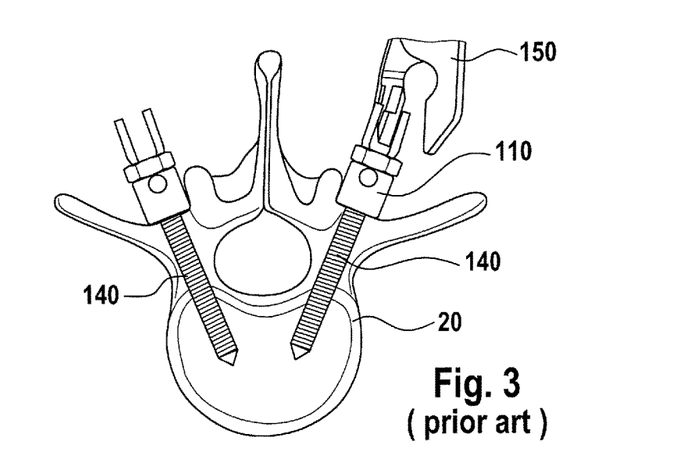
FIG. 3 shows known fixation devices attached to a vertebra.

FIG. 2 shows a top view of a vertebra to serve as a reference for the following description. In FIG. 2, the different portions of the vertebra are identified. FIG. 3 shows a top view of a vertebra 20 similar to FIG. 2. In FIG. 3, however, two devices 110 have been attached to the vertebra 20. The devices 110 are attached to the vertebra 20 by means of a respective screw 140, which runs through the pedicle and the body of the vertebra 20. In common techniques for spinal fixation, usually a tool, generally indicated by reference numeral 150 in FIG. 3, is used to fix the screw 140 to the vertebra 20.

Figure 4:
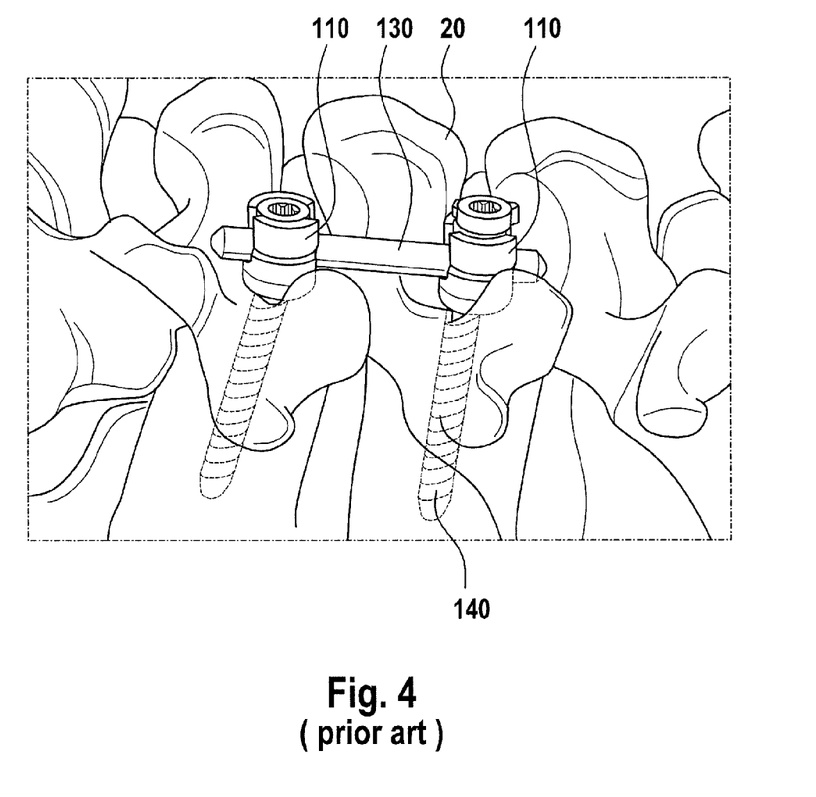
FIG. 4 shows a perspective view of a fixation system attached to vertebrae.

FIG. 4 shows a perspective view of a portion of a known spinal fixation system comprising two devices 110. The devices 110 are attached to different vertebrae 20 by means of a respective screw 140. Moreover, a rod 130 is connected between the devices 110 to anchor the vertebrae 20 to each other.

U.S. Pat. No. 8,162,946 B2 to Bacelli et al. discloses a surgical system for stabilizing a portion of a spine. The system comprises a spinal rod, an implant and an instrument. The instrument comprises a shaft, a moving part and a holder. The implant comprises a flexible tie and a bearing for bearing against the rod.

Moreover, U.S. Pat. No. 8,430,918 B2 to Bacelli et al. discloses a vertebral fixing system suitable for being mounted on a vertebra of the spine for connecting it to a rod. The system includes a connecting part suitable for being connected to the rod, a flexible ligature of elongated shape having two free ends suitable for connecting together the connecting part and at least a portion of a vertebra or a rib, and an adjustable locking member mounted on the connecting part.

In addition, US patent application No. 2009/0248077 A1 to Johns discloses a spine stabilization for the prophylactic treatment of adjacent level disease. A first vertebral level may be fused by advancing a pedicle screw in the first and second vertebra and coupling the bone screws to a rigid portion of a rod. A conformable ligature may be passed around a non-pedicle portion of a third vertebra and coupled to a dynamic portion of the rod using a blocking body.

However, known devices are usually difficult to attach to a vertebra and have the risk of causing damage to the spine.

It was therefore an objective of the present disclosure to provide a device that offers additional support to limit the compression on affected vertebrae while still offering a wide range of motion. It was a further objective to minimize the risk of damaging the spinal cord and the spinal roots when mounting the device to a vertebra during a surgical procedure. It was a further objective to provide a device that may easily be attached to a vertebra, and that may preferably be applied by the surgeon without requiring assistance to handle the device during the attachment process. It is a further objective of the present disclosure to allow a correction of the position of the implant after having attached the device to the vertebra.

SUMMARY OF THE INVENTION

The present disclosure solves the above-identified problems by providing a spinal fixation device according to appended claim 1. Particular embodiments are addressed in the depending claims.

The present disclosure provides a spinal fixation device comprising a body member having a first side and an opposite second side, and an elongate flexible strap having a first section and a second section. The first section of the strap is attached or attachable to attachment means of the body member arranged at a first location thereof. The second section of the strap is further sized and shaped to pass through a passageway arranged at a second location of the body member. The strap has a series of teeth and the passageway of the body member has a latch configured for engaging one of the teeth. The teeth and the latch are configured to allow a movement of the second section of the strap through the passageway in a tightening direction from the first side to the second side of the body member, and to prevent a movement of the second section in the opposite direction.

To apply the spinal fixation device to a vertebra of a patient, such as a human being or an animal, the body member of the device may be positioned against the vertebra, and the strap may be arranged to extend from the attachment means of the body member, around a portion of the vertebra, and through the passageway of the body member. As the second section of the strap may only be pulled through the passageway in the tightening direction, but not in the opposite direction, the spinal fixation device may easily be attached to the vertebra by pulling the second section further through the passageway to reduce the length of the strap between the attachment means and the passageway. To tighten the strap around the vertebra, no further instruments are needed. Rather, the surgeon may easily and conveniently pull the second section further through the passageway for fixation. To this effect, he or she may grip a portion of the second section of the strap that extends on the second side of the body member. Moreover, the risk of causing damage to the spinal cord or the spinal roots is reduced.

In some embodiments, the first and the second location may be separate. For example, the first location and the second location may be spaced apart by at least 5 mm, preferably at least 10 mm.

The passageway may be in the form of a through hole extending through the body member. The passageway may be, e.g., in the form of a slit. In particular, the passageway may extend from the first side of the body member to the second side of the body member. The latch may, e.g., be arranged in the passageway, at an end of the passageway or on the first or second side of the body member.

In some embodiments, the body member further comprises connecting means arranged on the second side thereof. The connecting means may be configured for connecting the spinal fixation device to another device. In particular, the connecting means may comprise a threaded bore. A threaded bore provides a convenient way of connecting the spinal fixation device to another device having a correspondingly threaded rod, such as, e.g., a screw. In these embodiments, the threaded bore may have inner threads matching the outer threads provided on the threaded rod. The threaded bore and the threaded rod may, e.g., be tapered.

In some embodiments, the connecting means are arranged between the first location and the second location of the body member. These embodiments allow the forces acting on the connecting means to be more evenly distributed between the first and the second location of the body member. The risk of dislocating the spinal fixation device either during the surgical procedure or thereafter is therefore reduced.

In some embodiments, the spinal fixation device further comprises a connection element having connecting means configured for attaching to the connecting means of the body member, and further having coupling means for attaching a connecting rod. In particular, the connecting means of the connection element may be arranged at an end section thereof, and the connection element may define a longitudinal axis. The coupling means of the connection element may be configured for attaching the connecting rod in an orientation transversely, in particular perpendicularly or substantially perpendicularly to the longitudinal axis of the connection element.

In some embodiments, the teeth are provided on a first side of the second section of the strap facing the attachment means when the second section extends through the passageway of the body member. The teeth may thus be provided on a first side of the strap that faces towards the body member when the strap is attached to the body member. In this embodiment, the teeth are in an orientation towards the vertebra, providing additional stabilization and avoiding damage to soft tissue surrounding the vertebra. Accordingly, a second side of the strap that is opposite the first side may be flat, e.g., free of any protrusions.

The teeth may further, e.g., have a triangular cross section. In some embodiments, each of the teeth may have two sides, each side defining an angle of inclination with respect to the longitudinal direction of the strap that is smaller than 90°. Alternatively or additionally, the cross section of the teeth may define an angle bisector that defines an angle with respect to the longitudinal direction of the strap that is smaller than 90°.

In some embodiments, the attachment means comprise a further passageway through the body member. In these embodiments, the first section of the strap may have a widening part that is sized and shaped to prevent a passage of the widening part through the further passageway of the body member. Alternatively, the first section of the strap may be attached to a widening element that is sized and shaped to prevent a passage of the widening element through the further passageway of the body member. The widening part of the first section of the strap or the widening element, respectively, may, in particular, be arranged over the second side of the body member, between the further passageway and the second side of the body member, and/or within the further passageway.

In some embodiments, the attachment means further comprise a first threaded bore extending from the second side of the body member to a position in the further passageway. The first threaded bore may, in particular, extend transversely to the further passageway. The spinal fixation device may further comprise a first screw configured for extending through the first threaded bore and into the further passageway, such that the first section of the strap is clamped between an end section of the first screw and an inner surface of the further passageway. The first screw may have outer threads matching the inner threads of the first threaded bore. In these embodiments, the first section of the strap may easily be fixedly clamped inside the further passageway to prevent a passage of the first section through the further passageway. In some embodiments, the widening part or the widening element comprises a cylinder.

In some embodiments, the attachment means comprise a further latch configured for engaging one of a further series of teeth provided on the strap, e.g., on the first side of the strap. In particular, the further latch and the further series of teeth may be configured for allowing a movement of the first section of the strap through the further passageway in a direction from the second side of the body member to the first side of the body member, and to prevent a movement of the first section of the strap in the opposite direction. The further series of teeth may, e.g. have a triangular cross section. The further series of teeth may be inclined with respect to the longitudinal direction in an opposite direction as compared with the series of teeth. In some embodiments, each of the further series of teeth may have two sides, each side defining an angle of inclination with respect to the longitudinal direction of the strap that is greater than 90°. Alternatively or additionally, the cross section of the further series of teeth may define an angle bisector that defines an angle with respect to the longitudinal direction of the strap that is greater than 90°. In these embodiments, the further series of teeth may be provided on the first section and series of teeth may be provided on the second section of the strap. In some embodiments, teeth may be provided along an entire length of the strap.

In some embodiments, the spinal fixation device further comprises locking means for locking the second section of the strap in the passageway of the body member. In particular, the locking means may be adapted for clamping the second section of the strap in the passageway of the body member.

In some embodiments, the locking means may comprise a second threaded bore extending from the second side of the body member to a position in the passageway, and the second threaded bore may extend transversely to the passageway. In particular, the spinal fixation device may further comprise a second screw configured for extending through the second threaded bore and into the passageway, such that the second section of the strap is clamped between an end section of the screw and an inner surface of the passageway. The second screw may have outer threads matching the inner threads of the second threaded bore.

In some embodiments, the spinal fixation device further comprises a cover configured to be attached to the second side of the body member. The cover may, for example, be configured to cover grooves, bores and holes provided on the second side of the body member.

In some embodiments, the cover is configured for clamping the second section of the strap between the second side of the body member and the cover to prevent a movement of the second section of the strap. Additionally or alternatively, the cover may be configured for clamping the first section of the strap between the second side of the body member and the cover to prevent a movement of the first section of the strap.

In some embodiments, the strap is made of a biocompatible plastic material or a metal sheet, such as titanium or another biocompatible metal material.

In some embodiments, the series of teeth comprises at least five, in particular at least ten teeth arranged along a longitudinal direction of the strap, such that the second section of the strap is attachable at the second location of the body member in at least five, in particular at least ten different positions.

BRIEF DESCRIPTION OF FIGURES

Further features and benefits of the present disclosure will be apparent to the skilled person when reading the following detailed description in conjunction with the appended figures, in which like reference numerals refer to like elements, and in which.

DETAILED DESCRIPTION

Figure 5:
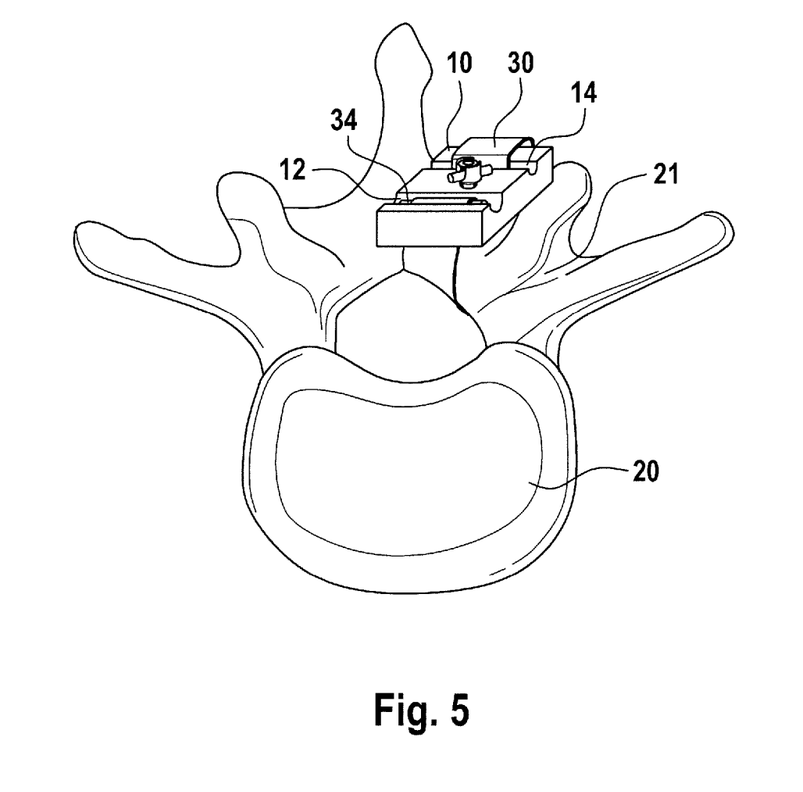
FIG. 5 shows a schematic drawing of a spinal fixation device according to an embodiment attached to a vertebra.

FIG. 5 shows a schematic view of a spinal fixation device according to an embodiment. The device comprises a body member 10 and a strap 30. The body member 10 may, e.g., be made of a solid material, such as a metal or a biocompatible plastic material. The body member 10 may be positioned against the vertebra 20, in particular, against a lamina 21 of the vertebra 20. The strap 30 extends from a first location of the body member 10 around the lamina 21 and back to a second location of the body member 10. As will be described in more detail below with reference to the following figures, a first and a second passageway are provided in the body member 10 at the first and second locations, respectively, to receive a first and a second section of the strap 30, respectively. A widening element 34 in the form of a cylinder is attached to a first end of the strap 30, e.g., by welding, glue or cold pressing. The cylinder 34 rests in a groove 12 formed at the first location on the second side of the body member 10, as shown in more detail in FIG. 6. The widening element 34 prevents passage of the first end of the strap 30 through the first passageway in the body member 10. The strap 30 can therefore not be pulled entirely through the first passageway, such that there is no need for an external device to hold the end of the strap 30 in place during the surgical procedure. The strap 30 passes through the first passageway, passes under the lamina 21, reenters the body member 10 through the second passageway and gets out through a groove 14 formed at the opening of the second passageway on the second side of the body member 10, as also shown in FIG. 6.

Figure 6:
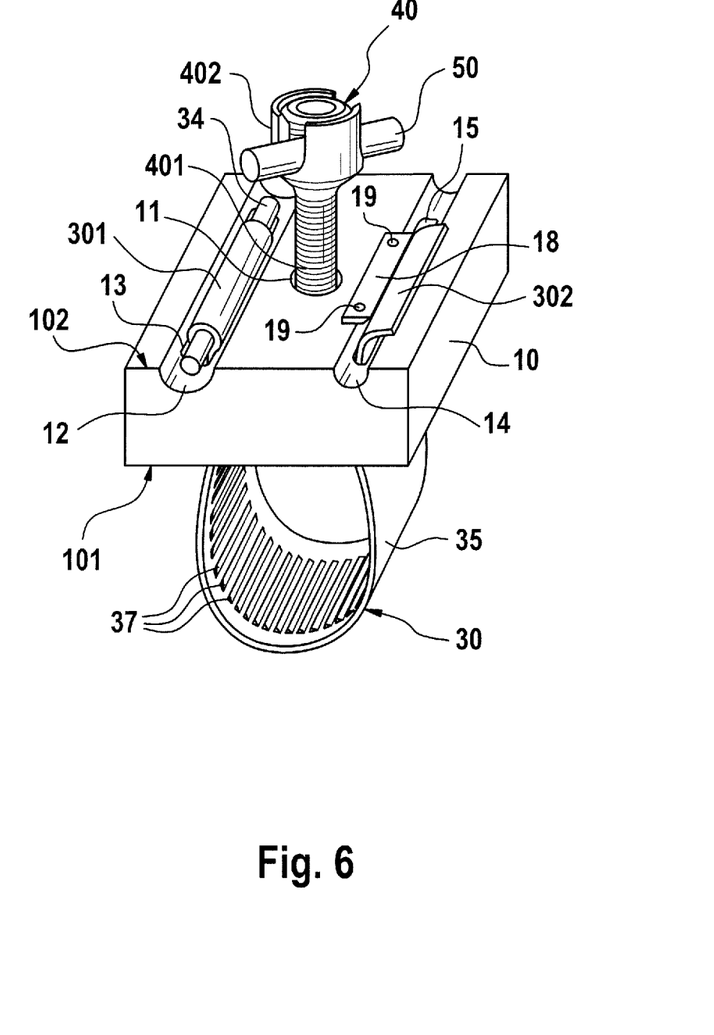
FIG. 6 shows a perspective view of a spinal fixation device according to an embodiment.

FIG. 6 shows a perspective view of the spinal fixation device of FIG. 5. As previously described, the body member 10 may be mounted on the lamina 21 of a vertebra 20 by means of the flexible strap 30. The body member 10 has a first side 101 and an opposite second side 102. Two passageways 13, 15 in the form of slit-shaped through-holes extend through the body member 10 from the first side 101 to the second side 102. A first passageway 13 ends in a first groove 12 arranged on the second side 102 of the body member 10. Similarly, a second passageway 15 ends in a second groove 14 arranged on the second side 102 of the body member 10. The strap 30 has a first section 301 located at a first end thereof. The first section 301 of the strap 30 is attached on one side to a cylinder 34, e.g., by welding, glue or cold pressing. The cylinder 34 rests in the groove 12. The strap 30 passes through the first passageway 13. The cylinder 34 attached to the first section 301 of the strap 30 is sized and shaped to prevent a passage of the first section 301 through the first passageway 13.

Starting from the cylinder 34 attached to the first section 301, the strap 30 extends through the first passageway 13 and forms a loop section 35 that is located on the first side 101 of the body member 10. A second section 302 of the strap 30 extends through the second passageway 15 in the body member 10. The first section 301 of the strap 30 may be at least partially wound around the widening element 34. A first side of the strap 30 is provided with a series of teeth 37 along a longitudinal direction of the strap 30. Each tooth 37 extends transversely, in particular perpendicularly to the longitudinal direction of the strap 30. A latch 18 is provided on the second side 102 of the body member 10 above the second groove 14 and is fixed by means of screws 19. The latch 18 is configured to engage the teeth 37 provided on the first side of the strap 30. In more detail, the latch 18 is provided on a side of the second groove 14 that faces towards the first groove 12. To tighten the strap 30 around the lamina 21 of a vertebra 20, a portion of the second section 302 of the strap that is located above the second side 102 of the body member 10 may be gripped by the surgeon and may easily be pulled away from the body member 10, causing a movement of a portion of the strap 30 through the passageway 15 from the first side 101 to the second side 102 of the body member 10. The engagement between the latch 18 and the teeth 37 further prevents a passage of the strap 30 through the passageway 15 in a reverse direction from the second side 102 to the first side 101 of the body member 10.

Moreover, the body member 10 comprises connecting means 11 in the form of a threaded hole or bore. In the embodiment shown in FIG. 6, the device further comprises a connecting element 40 having a threaded end section 401 with outer threads that match the inner threads of the threaded hole 11. The connecting element 40 further has a second end section 402 defining a passageway adapted to receive a connecting rod 50. The passageway in the end section 402 is arranged, such that the connecting rod 50, when received in the passageway, extends transversely, in particular perpendicularly to a longitudinal axis of connecting element 40. The connecting element 40 and the rod 50 may be used to connect the spinal fixation device with other spinal fixation devices that are, e.g., attached to adjacent vertebrae.

Figure 7:
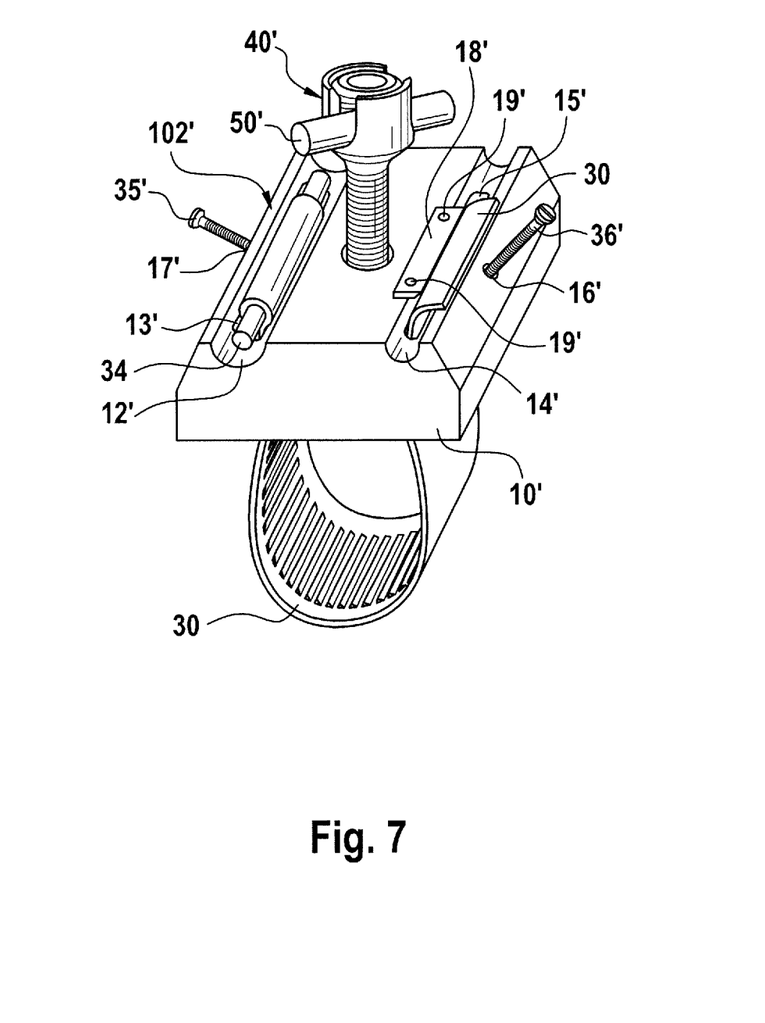
FIG. 7 shows a perspective view of a spinal fixation device according to an embodiment.

FIG. 7 shows a perspective view of a similar spinal fixation device as the one shown in FIG. 6. To avoid repetitions, in the following, only the differences between the embodiments of FIGS. 6 and 7 will be discussed. In addition to the features shown in FIG. 6, the device of FIG. 7 further has threaded bores 16', 17' that extend from the second side 102' of the body member 10'. Threaded bore 17' extends from the second side 102' of the body member 10' to a position in the first passageway 13', as is shown in more detail in FIG. 11. By fastening a screw 35' in the threaded bore 17', the strap 30 may be fixedly clamped between an end section of the screw 35' and an inner surface of the first passageway 13'.

Figure 11:
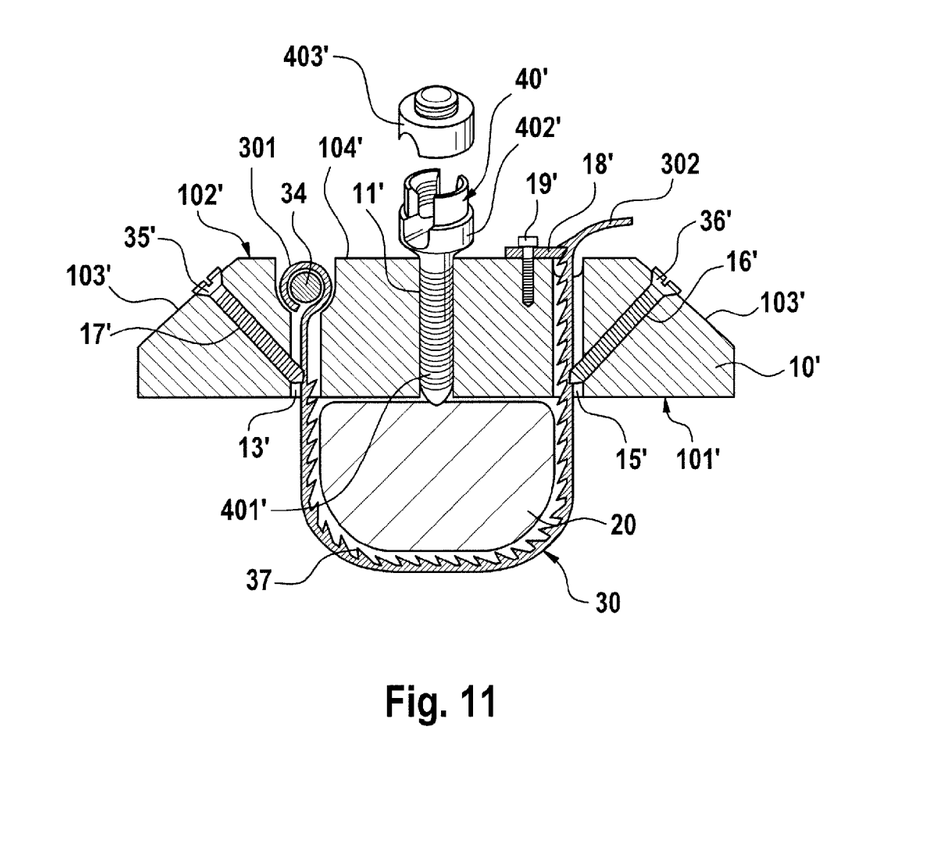
FIG. 11 shows a schematic cross-section of the spinal fixation device of FIG. 7.

Similarly, threaded bore 16' extends from the second side 102' of the body member 10' to a position in the second passageway 15' (see also FIG. 11). By fastening a screw 36' into the threaded bore 16', the strap 30 may be clamped by an end section of the screw 36' and an inner surface of the second passageway 15'. By clamping the strap 30 inside the passageways 13', 15', the strap 30 may be fixated in its final position, i.e., after pulling the second section 302 of the strap 30 through the second passageway 15' until the strap 30 runs tightly around the lamina 21 of the vertebra 20.

Figure 8:
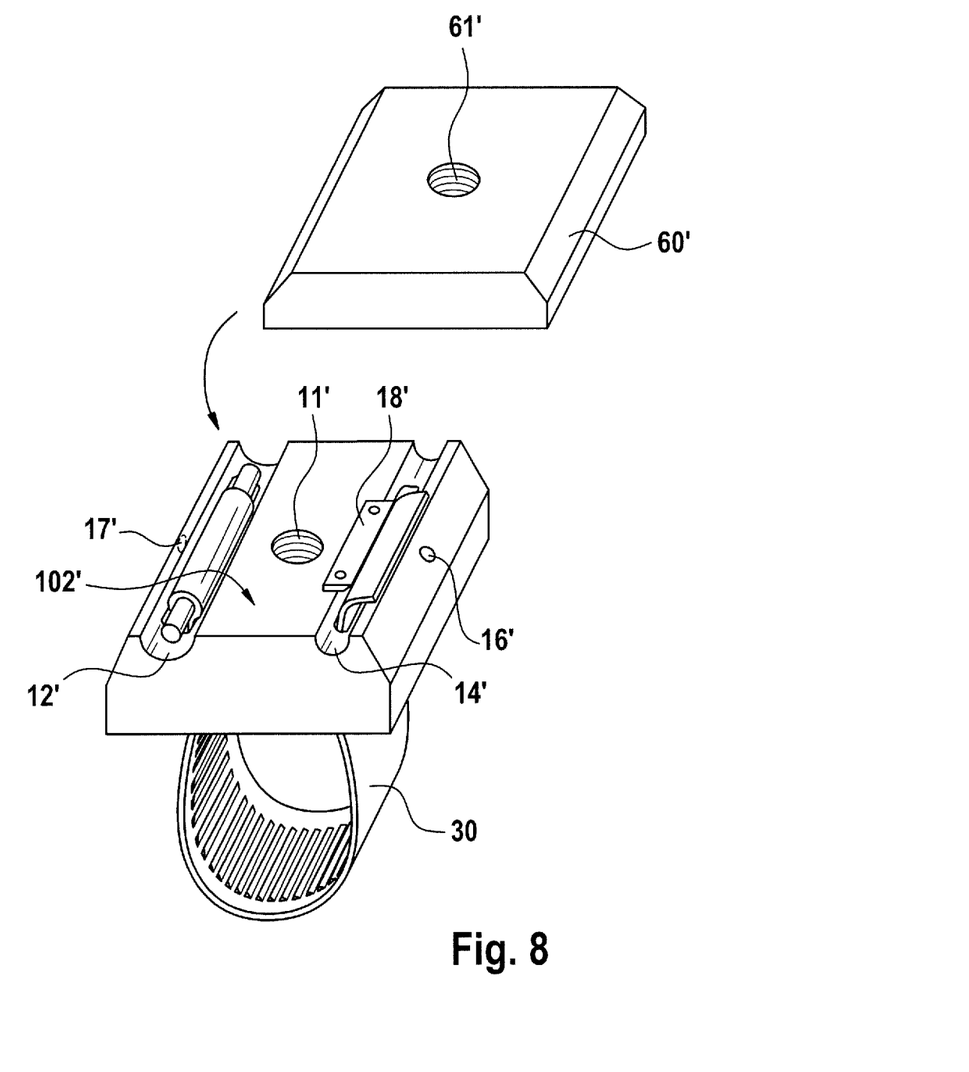
FIG. 8 shows an exploded view of the spinal fixation device of FIG. 7 having a cover.

FIG. 8 shows an explosion view of the spinal fixation device of FIG. 7, which further includes a cover 60'. The cover 60' is attachable to the second side 102' of the spinal fixation device to cover the grooves 12', 14' and the end sections 301, 302 of the strap 30 extending over the second side 102' of the body member 10'. The cover 60' has a central opening 61' which can be aligned with the connecting means, such as, e.g., the threaded hole 11' defined in the body member 10', when attached to the body member 10'. The cover 60' may be adapted to additionally clamp the first and second sections 301, 302 of the strap 30 between the cover 60' and the second side 102' of the body member 10'.

Figure 9:
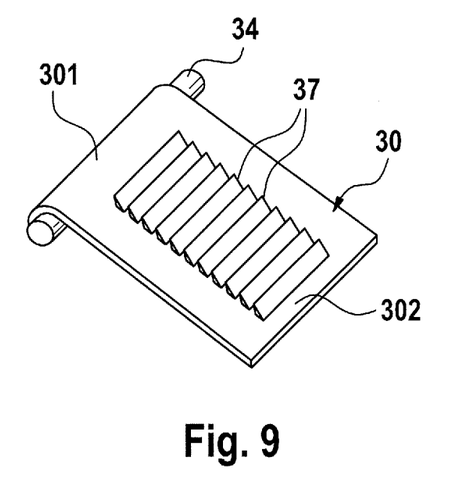
FIG. 9 shows a perspective view of a strap of a spinal fixation device according to an embodiment.

FIG. 9 is a perspective view of the strap 30. A widening element 34 in the form of a cylinder is attached to the first section 301 of the strap 30. The cylinder 34 extends perpendicularly to the longitudinal direction of the strap 30. A length of the cylinder 34 is greater than a width of the strap 30. Therefore, passage of the cylinder 34 through the passageway 13, 13' in the body member 10, 10' may be prevented, while still allowing a passage of the strap 30. A first side of the strap 30 is provided with a series of teeth 37. The teeth 37 extend perpendicularly to the longitudinal direction of the strap 30. The teeth 37 are angled away from a second end section 302 of the strap towards the first end section 301. The teeth 37 are thus configured for allowing a one-way movement of the strap 30 through the passageway 15, 15' of the body member 10 by engaging the latch 18, 18' of the body member 10, 10'.

Figure 10:
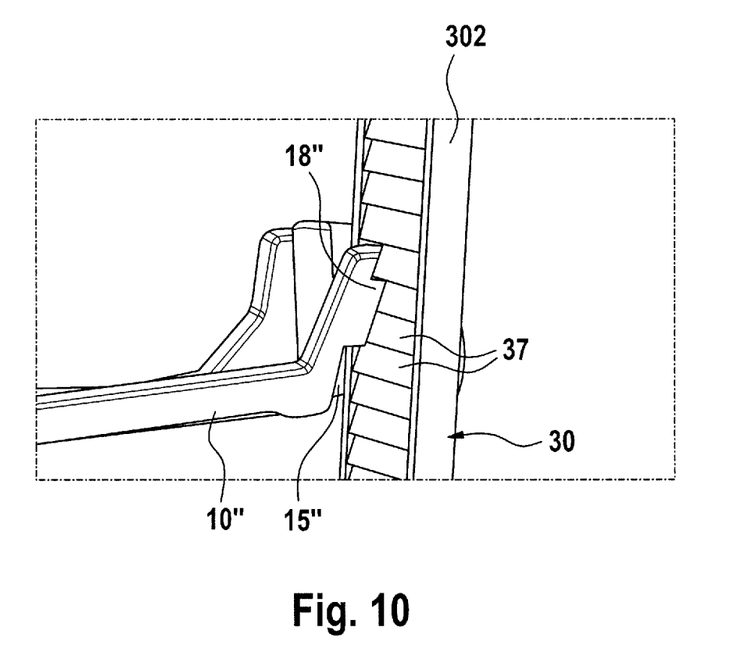
FIG. 10 shows a perspective partial view of a spinal fixation device according to an embodiment.

FIG. 10 shows a photograph of a portion of a spinal fixation device according to an embodiment. FIG. 10 shows a second section 302 of the strap 30 that extends through a passageway 15" in the body member 10". The body member 10" is provided with a latch 18" that is configured to engage one of a series of teeth 37 provided on the first side of the strap 30.

FIG. 11 shows a cross sectional view through the spinal fixation device of FIG. 7 that is attached to a lamina of a vertebra 20. As can be seen from FIG. 11, the second side 102' of the body member 10' has a flat central portion 104' that extends parallel to the first side 101' of the body member 10'. The second side 102' further has peripheral portions 103' that are angled with respect to the central portion 104'. The threaded bores 16', 17' extend from a respective one of the peripheral portions 103' of the second side 102' to a respective position in the respective passageway 13', 15', as described in more detail above. The latch 18' is provided on the second side 102' of the body member 10' above the passageway 15' and is fixed by means of screws 19'.

As can also be seen from FIG. 11, the teeth 37 provided on the first side of the strap 30 are angled towards the first section 301 of the strap. In more detail, each of the teeth 37 provided on the second section 302 has two sides, each side defining an angle of inclination with respect to the longitudinal direction of the strap 30 that is smaller than 90°, and the cross section of the teeth 37 defines an angle bisector that defines an angle with respect to the longitudinal direction of the strap 30 that is smaller than 90°. This way, the second section 302 may easily be pulled through the passageway 15' in the body member 10' from the first side 101' to the second side 102', while a movement of the second section 302 through the passageway 15' in the opposite direction is prevented. Hence, the strap 30 may easily be tightened around a lamina 21 of the vertebra 20 by pulling a portion of the second section 302 that is located above the second side 102' of the body member 10' away from the body member 10'. After the strap 30 has thus been tightened around the lamina 21 of the vertebra 20, the latch 18' and the teeth 37 prevent a loosening movement of the strap 30, i.e. a passage of the second section 302 through the passageway 15' from the second side 102' towards the first side 101' of the body member 10'. In this position, the strap 30 may further be fixated by screws 34', 35' that are inserted and fastened in the threaded bores 16', 17'.

As shown in FIG. 11, the connecting element 40' further comprises a stem portion 402' and a removable cap 403'. The stem portion 402' has an end section 401' with outer threads matching the inner threads of the threaded hole of the body member 10' that serves as connecting means 11'. The cap 403' is further adapted to be screwed onto a further end section of the stem portion 402', and to define a passageway for a connecting rod (not shown) between the stem portion 402' and the cap 403'.

Figure 12:
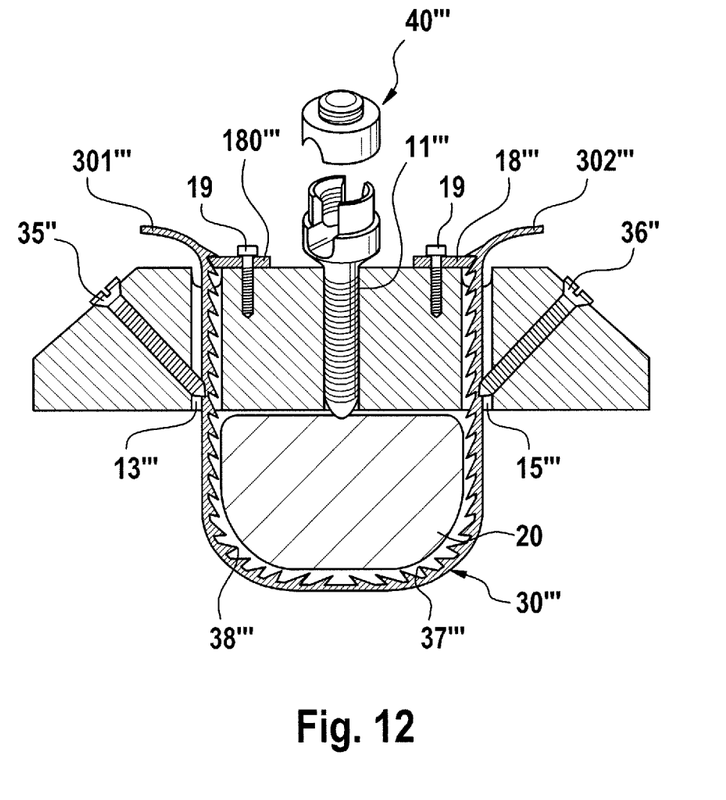
FIG. 12 shows a schematic cross-section of a spinal fixation device according to an embodiment.

While FIG. 11 shows a cylinder 34 attached to the first section 301 of the strap 30, the skilled person will understand that the first section 301 of the strap 30 may alternatively or additionally include a widening part that is sized and shaped to prevent a passage of the widening part through the passageway 13, 13'. The skilled person will further understand that the first section of the strap may be fixed to the body member by other means. For example, as shown in the embodiment of FIG. 12, a second latch 180''' may be arranged above the first passageway 13''', e.g., by means of screws 19. The latch 180''' is configured to engage additional teeth 38''' provided on the first section 301''' of on the strap 30''' to prevent a movement of the first end section 301''' of the strap 30''' through the passageway 13''' from the second side 102''' to the first side 101''' of the body member 10''', and to allow a movement in the opposite direction. The additional teeth 38''' are angled with respect to a longitudinal direction of the strap 30''' in an opposite direction as compared to the teeth 37''' provided on the second section 302''' of the strap 30'''. The additional teeth 38''' further have a triangular cross section. Each of the additional teeth 38''' has two sides, each side defining an angle of inclination with respect to the longitudinal direction of the strap 30''' that is greater than 90°, and the cross section of the additional teeth 38''' defines an angle bisector that defines an angle with respect to the longitudinal direction of the strap 30''' that is greater than 90°. Similarly, each of the teeth 37''' provided on the second section 302''' has two sides, each side defining an angle of inclination with respect to the longitudinal direction of the strap 30''' that is smaller than 90°, and the cross section of the teeth 37''' defines an angle bisector that defines an angle with respect to the longitudinal direction of the strap 30''' that is smaller than 90°.

It will be evident to the skilled person that modifications, variations and substitutions of the features of the described embodiments are possible.

We claim:

1. A spinal fixation device comprising a body member having a first side and an opposite second side, and an elongate flexible strap having a first section and a second section, wherein the first section of the strap is at least partially wound around a widening element, the widening element being sized and shaped to prevent a passage of the first section of the strap through a passageway arranged at a first location of the body member, wherein the second section of the strap is further sized and shaped to pass through a passageway arranged at a second location of the body member, wherein the strap has a series of teeth and the passageway at the second location of the body member has a latch configured for engaging one of the teeth, the teeth and the latch being configured to allow a movement of the second section of the strap through the passageway at the second location in a tightening direction from the first side to the second side of the body member, and to prevent a movement of the second section in the opposite direction, wherein the body member further comprises connecting means, arranged on the second side thereof, receiving a connecting element, and wherein the connecting element has a first end section engaged with the connecting means of the body member and a second end section disposed above the second side of the body member and adapted to receive a connecting rod to couple the spinal fixation device to one or more spinal fixation devices attached at different positions in the spine.

2. The device of claim 1, wherein the passageway at the second location is in the form of a through hole through the body member.

3. The device of claim 1, wherein the connecting means comprises a threaded bore.

4. The device of claim 1, wherein the connecting means is arranged between the first location and the second location of the body member.

5. The device of claim 1, wherein the connecting element defines a longitudinal axis and wherein the second end section of the connecting element is configured to receive the connecting rod in an orientation transverse to the longitudinal axis.

6. The device of claim 1, wherein the teeth are provided on a first side of the second section of the strap facing the attachment means when the second section extends through the passageway at the second location of the body member.

7. The device of claim 6, wherein a second side of the strap that is opposite the first side is flat.

8. The device of claim 1, further comprising an attachment means for fixing the first section of the elongate flexible strap in the passageway arranged at the first location of the body member.

9. The device of claim 8, wherein the attachment means comprises a first threaded bore extending from the second side of the body member to a position in the passageway at the first location, and wherein the first threaded bore extends transversely to the passageway at the first location.

10. The device of claim 9, further comprising a first screw configured for extending through the first threaded bore and into the passageway at the first location, such that the first section of the strap is fixed in the passageway at the first location by being clamped between an end section of the first screw and an inner surface of the passageway at the first location.

11. The device of claim 1, wherein the widening element comprises a cylinder.

12. The device of claim 1, further comprising locking means for locking the second section of the strap in the passageway at the second location of the body member.

13. The device of claim 12, wherein the locking means comprises a second threaded bore extending from the second side of the body member to a position in the passageway at the second location, and wherein the second threaded bore extends transversely to the passageway at the second location.

14. The device of claim 13, further comprising a second screw configured for extending through the second threaded bore and into the passageway at the second location, such that the second section of the strap is locked in the passageway at the second location by being clamped between an end section of the second screw and an inner surface of the passageway at the second location.

15. The device of claim 1, further comprising a cover configured to be attached to the second side of the body member.

16. The device of claim 15, wherein the cover is configured for clamping the second section of the strap between the second side of the body member and the cover to prevent a movement of the second section of the strap.

17. The device of claim 1, wherein the strap is made of a biocompatible plastic material or a metal sheet.

18. The device of claim 1, wherein the series of teeth comprises at least five teeth arranged along a longitudinal direction of the strap, such that the second section of the strap is attachable at the second location of the body member in at least five different positions.

* * * * *